United States Patent [19]

Jackson et al.

[11] Patent Number: 5,132,233
[45] Date of Patent: Jul. 21, 1992

[54] SAMPLE INJECTION CELL

[75] Inventors: Delbert D. Jackson, Placentia; Samuel G. Ricchio, Fullerton, both of Calif.

[73] Assignee: Beckman Instruments, Inc., Fullerton, Calif.

[21] Appl. No.: 322,813

[22] Filed: Mar. 13, 1989

[51] Int. Cl.⁵ .................................................. G01N 35/00
[52] U.S. Cl. .................................. 436/179; 73/864.81; 73/864.85; 422/63; 422/100; 436/49; 436/51; 436/52; 436/53; 436/54; 436/174; 436/180
[58] Field of Search ............... 436/49, 51, 52, 53, 436/54, 179, 174, 180; 73/864.85, 864.87; 422/62, 63, 68, 70, 75, 81, 100

[56] References Cited

U.S. PATENT DOCUMENTS

| 3,186,799 | 6/1965 | Hach | 23/253 |
|---|---|---|---|
| 3,327,520 | 6/1967 | Stapp . | |
| 3,419,358 | 12/1968 | Smythe et al. | 436/179 |
| 3,604,267 | 9/1971 | Johns | 73/422 GC |
| 3,647,386 | 3/1972 | Gilford | 436/179 |
| 3,719,086 | 3/1973 | Bannister | 73/423 A |
| 3,788,816 | 1/1974 | Rohrbaugh | 23/253 R |
| 3,869,068 | 3/1975 | Chen | 222/148 |
| 3,902,371 | 9/1975 | Hooper | 73/423 A |
| 3,911,749 | 10/1975 | Hendry | 73/423 |
| 3,964,864 | 6/1976 | Dahms | 23/230 B |
| 3,997,420 | 12/1976 | Buzza | 204/195 P |
| 4,019,861 | 4/1977 | Dahms | 23/230 B |
| 4,086,061 | 4/1978 | Hoffa | 23/259 |
| 4,170,523 | 10/1979 | Buzza | 204/1 T |
| 4,199,988 | 4/1980 | Riegger | 73/422 GC |
| 4,202,747 | 5/1980 | Buzza | 204/195 R |
| 4,218,197 | 8/1980 | Meyer | 417/422 |
| 4,259,289 | 3/1981 | Curry | 422/64 |
| 4,297,903 | 11/1981 | Buzza | 73/864.22 |
| 4,338,280 | 7/1982 | Ambers et al. | 422/81 |
| 4,399,711 | 8/1983 | Klein | 73/864.16 |
| 4,419,903 | 12/1983 | Jackson | 73/864.01 |
| 4,463,615 | 8/1984 | Buzza | 73/863.32 |
| 4,490,234 | 12/1984 | Buzza | 204/409 |
| 4,621,534 | 11/1986 | Munari | 73/864.86 |
| 4,705,667 | 11/1987 | Marsoner | 422/68 |
| 4,729,876 | 3/1988 | Hennessy et al. | 422/100 |
| 4,730,631 | 3/1988 | Schwartz | 422/63 |
| 4,865,993 | 9/1989 | Cassaday | 422/81 |

FOREIGN PATENT DOCUMENTS 2025900A 1/1980 United Kingdom .

OTHER PUBLICATIONS

*System E4A Operating Manual*, Beckman Instruments, Inc., Clinical Instruments Division, Brea, Calif., Section Three, Principles of Operation, pp. 3-1 through 3-8.

*Primary Examiner*—Timothy M. McMahon
*Attorney, Agent, or Firm*—William H. May; Arnold Grant; Gary T. Hampson

[57] ABSTRACT

The sample injection cell comprises a body and a bore through the body for receiving a probe to pass fluid sample into the bore. A transverse passageway into the body permits a diluent to enter the bore and be mixed with a sample in a predetermined ratio and be dispensed directly into the flow cell. The diluent simultaneously washes the probe when the probe is located in the bore. A waste basin forms part of an integral unit and is adjacent the bore so that fluid from a flow cell can enter the waste basin and then exit under gravity to a waste drain.

2 Claims, 1 Drawing Sheet

SAMPLE INJECTION CELL

RELATED APPLICATIONS

This invention relates to the inventions and disclosures which are the subject of application Nos.: 07/322,814 filed Mar. 12, 1989 07/322,802 filed Mar. 13, 1989 07/322,810 filed Mar. 13, 1989 07/322,811 filed Mar. 13, 1989 07/322,812 filed Mar. 13, 1989 07/322,807 filed Mar. 13, 1989. All these applications are filed contemporaneously with the present application and the contents of them all are incorporated by reference herein.

BACKGROUND

This invention relates to automatic analytical instruments. In particular, the invention is directed to an injection cell for injecting fluid samples into the instrument for analysis.

Different analyzers are available for automatic clinical chemistry analysis. The analyzers use different types of analytical procedures to obtain desirable attributes and advantages.

One particular kind uses a plurality of individual analysis modules having open reaction or sample cups. An automated sample probe withdraws a sample volume from samples in the sample cups carried on a carousel and distributes the sample fluid to analysis modules in accordance with tests selected by an instrument operator.

Another kind of analyzer uses a flow cell through which the sample and a diluent flows to determine electrolytes in the sample. This analyzer also uses a sample pick-up probe to extend into the sample cup to aspirate the sample into the probe. Thereafter, the sample is ejected or dispensed from the probe into an injection cell.

Drawbacks arise with existing designs of the injection cell and related probe. Periodic washing of the probe is required so that contamination from one sample to another sample does not occur. For this purpose, different washing stations are used into which the probe is periodically submitted. The washing station would be used between each test. The disadvantage of this is that a specific time period is necessary to effect the washing. This increases the time cycle necessary for analyzing multiple samples. Additionally, separate mechanisms and facilities need to be provided for the washing and the components for this often require pump means. This is relatively expensive and a drawback of existing injection cells.

The present invention seeks to overcome the drawbacks in the prior art.

SUMMARY

The present invention provides an injection cell for operation with a probe which overcomes the disadvantages of existing injection cells and probes. The injection cell provides for a single operation wherein a probe can eject or dispense sample fluid into an injection cell. A separate washing step for the probe, or a washing system, is not required.

According to the invention, a sample injection cell comprises a body, and a bore through the body for receiving a probe to pass fluid sample into the bore. A passageway for a diluent stream is provided to the bore to be mixed with the sample in the predetermined ratio with the fluid sample in the bore. The diluent simultaneously washes the probe surface when the probe is located in the bore. Outlet means from the bore permits exit of the fluid sample and the diluent from the injection cell.

The sample and diluent is directed from the injection cell to a flow cell of an analyzer.

The bore is elongated thereby to wash effectively the probe, which is also elongated, with diluent. The elongated bore increases the volume for mixing the fluid sample with the diluent. The passageway for diluent entry is preferably located adjacent the entry into the bore for the probe. This increases the length for diluent flow over the exterior surface of the probe when located in the bore. In this manner, the fluid sweeps down the exterior of the bore and washes the probe exterior. At the outlet tip of the probe, the diluent mixes with sample fluid ejected from the probe tip in a predetermined ratio. The fluid and diluent travel down the lower part of the bore together.

In a preferred form, the injection cell includes a waste basin located adjacent the bore in a single unit. The waste basin is connected with an outlet from the flow cell for fluid exiting from the flow cell.

The probe preferably includes a seal about an exterior surface of probe. The seal is for seating about an inlet port to the bore.

The invention is further described with reference to the accompanying drawings.

DRAWINGS

DESCRIPTION

Figure 1:
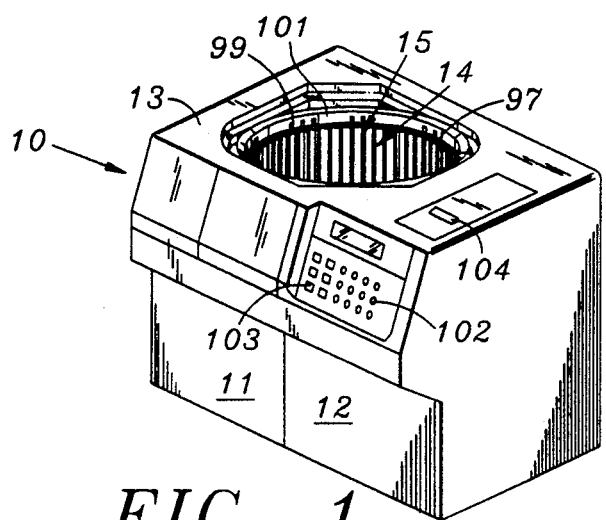
FIG. 1 is a perspective view of an automatic clinical analyzer of which the injection cell is a part.
Figure 3:
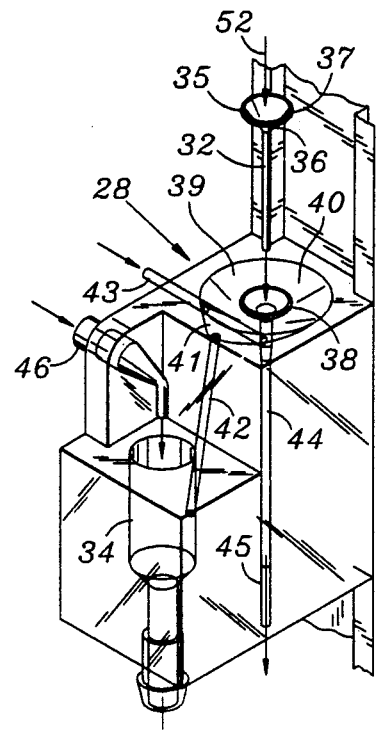
FIG. 3 is a perspective view of the injection cell with a probe illustrated above the injection cell.
Figure 2:
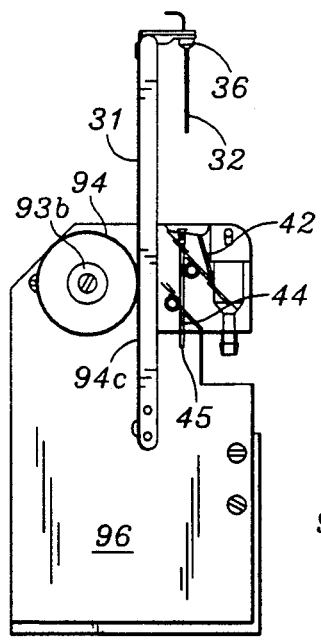
FIG. 2 is a side view of the injection cell in association with a crane for operating a probe in relationship with the injection cell.

An automatic clinical chemistry analyzer 10 includes a housing 11 with an open face top 12. Into the open face top 12 trough section there a trough section into which is fitted a sample wheel 13. The sample wheel 13 is driven by a drive wheel located about the outside periphery of the sample wheel 13. The sample wheel 13 includes discrete sample cups 14 arranged circumferentially about the periphery of the sample wheel 13. The sample cups 14 are either cups, tubes or vials and contain sample fluid to be analyzed in the analyzer 10.

Figure 4:
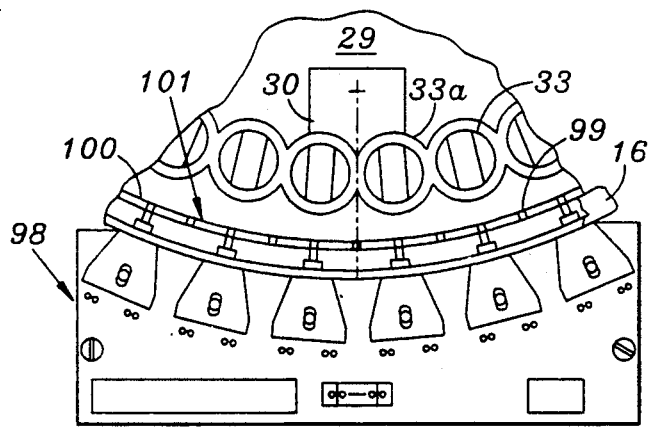
FIG. 4 is a partial plan view of a sample tray indicating sample reaction cups and a target location where the probe and injection cell operate relative to the sample cups.

Located strategically relative to the sample wheel 13, and at least partly within the perimeter formed by the reaction cups 14, is a target location 115. At the target location 115, there is mounted a crane 15, the mounting being below the surface of a base plate 16 of the trough formed in the top face 12 for receiving the sample wheel 13. The base plate 16 is shown diagrammatically in part in FIG. 4. The base plate 16 is below the bottoms of the reaction cups 14 of the sample wheel 13.

The crane 15 moves vertically upwardly and downwardly under the action of a motor 17 with a drive band 18 which wraps about a drive hub 19 mounted about a horizontal axis. This causes a probe 20 mounted at the uppermost position 22 of the crane 15 to move simultaneously upwardly and downwardly. The length of probe 20 is elongated so that the probe 20 can be located deep into bore 23 of an injection cell 24.

The injection cell 24 is mounted below the target region 115. The crane 15 moves above and below the base plate 16 to remove sample fluid from the sample cups 14 when the cups 14 are moved into position and aligned with the vertical motion of probe 20. This movement of the sample cups 14 is effected by a drive wheel mechanism for the sample wheel 13 of the clinical analyzer 11. When the sample cups 14 are removed from the vertical travel path of probe 20, the crane 15 causes the probe 20 to move below the base plate 16. The probe 20 ejects or dispenses fluid into the bore 23 of the injection cell 24 which is mounted below the plate 16.

The bore 23 includes an inlet port 25 and an outlet port 26 at the base of the body 27 constituting the injection cell 24. The diameter of the probe 20 is less than the diameter of the bore 23 so that probe 20 can easily be accommodated within the bore 23. Simultaneously, diluent entering through a transverse passageway 28 passes down the exterior of the probe 20 between the wall of the bore 23 when the probe 20 is located in the bore 23. The passageway 28 is substantially right angularly directed relative to the bore 23 and is located adjacent the inlet port 25 of the injection cell 27. In this manner, diluent fluid which enters through tube 29 connected to the passageway 28 in a direction along arrow 30 can sweep past the exterior surface of the probe 20 and effectively wash the exterior of the probe 20.

The diluent and sample fluid are ejected from the outlet 26 which is connected to a tube 31 and passes in a direction of arrow 32 to a flow cell 33.

The fluid sample enters the probe 20 through a conduit 62 connected to the inlet of probe 20 in the direction of arrow 63. After exiting from the flow cell 33, the fluid passes along a fluid path 44 and enters in the direction of arrow 45 into a port 46. From port 46 the fluid is deposited into a waste basin 47 as indicated by arrow 48. From the waste basin 47, there is an outlet port 49 located at the base of the injection cell 24 which is connected for gravity feeding to a drain 50 as indicated by arrow 51. The waste basin 47 and bore 23 may be formed as an integral unit in the injection cell 24.

There is a seal 52 around the probe 20. This seal 52 has a truncated conical section 53 and a circumferential rib 54 at the base and widest part of the truncated conical section 53. A mating truncated conical seat 55 is located at the inlet port 25 to the bore 23. A similar circular ring seat 56 is provided about the widest portion of the truncated conical section 55 to accommodate the rib 54. The truncated conical seat 55 is formed within a larger truncated funnel section 57 at the top face 58 of the injection cell 24.

The crane 15 moves downwardly to cause the probe 20 periodically to enter the port 25. A sufficient positive pressure or action is provided so that the seal 52 mates effectively with the mating face of seat 56. The fluid sample is thereby positively and without contamination, ejected or dispensed, into the injection cell 24.

Any overflow or excess fluid entering in the larger truncated funnel section 57 is ejected through the overflow passageway 158. This passageway 158 is connected between the funnel section 57 and the waste basin 47. The passageway 158 is integrally formed within the body constituting the injection cell 24. The injection cell 24 is formed of a transparent plastic or Lucite (Trademark) material so that fluid flow in the cell 24 is visible to an operator opening the doors 59 of the housing 11 of the analyzer 10.

The seal 53 is formed of soft rubber. The probe 20 is relatively longer than prior art probes in order to aspirate effectively fluids from the cups 14 into the bore 23 and in turn into a flow cell 33. The preferred size of the probe 20 is about $1 \times 40$ mm. A sufficient length 60 is provided in the bore 23 below location of tip 61 of the probe 20 to achieve an effective mixing volume in the injection cell 24. The preferred ratio of mixing between the diluent entering the bore 28 and the sample through probe 23 is about 20 parts diluent to 1 part sample. This high volume of diluent will therefore pass along the exterior of the probe 20 and the high volume will ensure effective sweep cleaning of the probe exterior. Accordingly, there is no need for a special washing step or system to wash the exterior of the probe 20.

The crane 15 is operated by the band 18 which is wrapped around the drive hub 19. The crane 15 moves vertically upwardly and downwardly as the drive hub 19 is directed by the motor 17. The band 18 is fastened at 65 to the vertical beam 64. The crane 15 is mounted on a mounting bracket 66 and the motor 17 is also mounted on the bracket 66. The location of the crane 15 and the injection cell 24 are determined relative to the target location 115 so that the probe 20 is operative between the injection cell 24 and sample cups 14 as required. Helical springs are anchored within crane 15 and act to tension the drive band during the upward and downward movement of the beam 64. Thus, the springs maintain the tension when the motor 17 is reversedly operable with minimum backlash.

The crane motion is simple with the minimum number of parts and elimination of components such as lead screws, drive belts and the like. The crane 15 moves only in a vertical manner without transverse motion. Similar band drive systems are used to operate other components in the clinical analyzer with the same operating technique Hence, streamlined production of the analyzer is facilitated.

The above description of the invention should be considered as illustrative only. Many other embodiments of the invention, each differing from others in matters of detail only. The invention should be considered in terms of the scope of the following claims.

We claim:

1. A method of injecting a sample into an injection cell having a body with a elongated bore through the body comprising inserting a elongated probe into the bore, the probe being coaxially directed relative to the bore to pass a fluid sample from the probe into the bore, adding a diluent into the bore, mixing the diluent with the sample exiting the probe in a predetermined ratio in the bore, and simultaneously washing an exterior surface of the probe with the diluent when the probe is located in the bore and wherein, when the probe is located in the bore for discharging the sample, the diluent and sample mix in a length of the bore below the probe including removing overflow fluid from an inlet to the bore to a waste basin via a passage way through said body.

2. A method as claimed in claim 1 including directing fluid from the cell to a flow cell, and directing an outlet from the flow cell to a waste basin adjacent the bore.

* * * * *